US011679081B2

(12) United States Patent
Thyresson et al.

(10) Patent No.: US 11,679,081 B2
(45) Date of Patent: Jun. 20, 2023

(54) CHEWING GUM COMPRISING NICOTINE

(71) Applicant: McNeil AB, Helsingborg (SE)

(72) Inventors: Kristina Thyresson, Lund (SE);
Gregory Koll, Hillsborough, NJ (US);
Jill Nilgard, Helsingborg (SE); Gerard McNally, Derwyn, PA (US); Katarina Lindell, Eslöv (SE)

(73) Assignee: McNeil AB, Helsingborg (SE)

( * ) Notice: Subject to any disclaimer, the term of this patent is extended or adjusted under 35 U.S.C. 154(b) by 0 days.

(21) Appl. No.: 17/258,834

(22) PCT Filed: Jul. 12, 2019

(86) PCT No.: PCT/EP2019/068882
§ 371 (c)(1),
(2) Date: Jan. 8, 2021

(87) PCT Pub. No.: WO2020/012009
PCT Pub. Date: Jan. 16, 2020

(65) Prior Publication Data
US 2021/0299040 A1    Sep. 30, 2021

(30) Foreign Application Priority Data
Jul. 13, 2018  (SE) .................................. 1850896-0

(51) Int. Cl.
| A61K 9/68 | (2006.01) |
| A61K 31/465 | (2006.01) |
| A61K 47/02 | (2006.01) |
| A61K 47/26 | (2006.01) |
| A61K 47/38 | (2006.01) |

(52) U.S. Cl.
CPC .......... *A61K 9/0058* (2013.01); *A61K 31/465* (2013.01); *A61K 47/02* (2013.01); *A61K 47/26* (2013.01); *A61K 47/38* (2013.01)

(58) Field of Classification Search
CPC .... A61K 31/465; A61K 9/0058; A61K 47/38; A61K 47/02; A61K 47/26
See application file for complete search history.

(56) References Cited

U.S. PATENT DOCUMENTS

| 5,665,406 A * | 9/1997 | Reed ...................... A23G 4/046 |
| | | 426/5 |
| 6,627,234 B1 | 9/2003 | Johnson et al. |
| 2004/0037879 A1 | 2/2004 | Adusumilli et al. |
| 2006/0275344 A1* | 12/2006 | Mody ..................... A61P 25/34 |
| | | 424/439 |
| 2007/0231435 A1 | 10/2007 | Ream et al. |
| 2012/0017924 A1* | 1/2012 | Lindell .................... A23G 4/20 |
| | | 424/440 |
| 2012/0039981 A1* | 2/2012 | Pedersen .................. A23G 4/12 |
| | | 424/440 |
| 2013/0209540 A1 | 8/2013 | Duggins et al. |
| 2013/0309292 A1 | 11/2013 | Andersen |

FOREIGN PATENT DOCUMENTS

| WO | 2002/102357 A | 12/2002 |
| WO | 2006/124366 A | 11/2006 |
| WO | 2007/133141 A | 11/2007 |
| WO | 2009/007768 A | 1/2009 |
| WO | 2009/080021 A | 7/2009 |
| WO | 2010/044736 A | 4/2010 |
| WO | 2013/091631 A | 6/2013 |
| WO | 2013/119627 A | 8/2013 |

OTHER PUBLICATIONS

SE Search Report and Examination Report dated Feb. 20, 2019, for SE 1850896-0.
International Search Report and Opinion dated Sep. 11, 2019 for PCT/EP2019/068882.
Charkevich, D.A, *Pharmakologia*, Textbook. M.: GEOTAP—Media, 2008, p. 66-67.
Krosnjuka, I.I. et al., *Pharmacevticheskaja technologija*, Textbook. M.: Akademija, 2006, p. 42, 83.
Tentzova, A.I. et al.: "Modern biopharmaceutical aspects of excipients", *Pharmazia*, 2012, No. 7, p. 3-6.

* cited by examiner

*Primary Examiner* — Doan T Phan

(57) ABSTRACT

The invention relates to a chewing gum comprising at least a gum core comprising nicotine polacrilex, at least a one outer coating covering the core, comprising at least one sugar alcohol or mixtures of sugar alcohols and, at least a one portion fused onto the outer coating, wherein the portion comprises nicotine bitartrate or nicotine ditartrate dihydrate and at least one sugar alcohol or a mixture of sugar alcohols and at least one buffer present in the coating and/or in a portion fused to the coating.

22 Claims, No Drawings

CHEWING GUM COMPRISING NICOTINE

CROSS-REFERENCE TO RELATED APPLICATIONS

This application is the national stage filing under 35 USC 371 of international application PCT/EP2019/068882 filed on Jul. 12, 2019, which claims priority to SE 1850896-0 filed on Jul. 13, 2018.

FIELD OF INVENTION

The invention relates to a chewing gum comprising at least a gum core comprising nicotine polacrilex, at least a one outer coating covering the core, comprising at least one sugar alcohol or mixtures of sugar alcohols and, at least a one portion fused onto the outer coating, wherein the portion comprises nicotine bitartrate or nicotine ditartrate dihydrate and at least one sugar alcohol or a mixture of sugar alcohols and at least one buffer present in the coating and/or in a portion fused to the coating.

BACKGROUND OF INVENTION

According to WHO about six million people die from smoking each year, even though there are products on the market to help a smoker to quit smoking, products such as chewing gums, patches, lozenges and sprays.

A traditional way to produce a nicotine chewing gum is to create a complex of nicotine with a cation exchange resin and add the complex to a chewing gum.

Such chewing gums are available on the market since many years, sold under for example the trade mark Nicorette®. However, there are still consumers that are looking for products that will give faster craving relief profile, closer to the craving relief profile of a cigarette and thus there is a need of developing new nicotine chewing gums that satisfy a population of people that need a faster release of nicotine. Consumers are looking for products that are not too expensive and/or products that are could be non-visible upon use.

WO2006124366 discloses a chewing gum comprising nicotine polacrilex within the core onto which is applied at least one inner polymer film coating and thereafter onto which is applied at least one outer hard coating. The gums provide nicotine to the human being in an extended release form, see example 1 in the application. Nothing teaches a person skilled in the art to use two different forms of nicotine to be able to create an immediate and extended release of nicotine.

WO2013119627 discloses medicated chewing gums, but nothing about how to create a chewing gum or the technical problems having an immediate and extended release of nicotine from a chewing gum.

One product on the market giving rise to a fast craving release is the Nicorette™ QuickMist™ which is a mouth spray to be applied to the oromucosa from which the nicotine compound is readily absorbed into the blood stream to give a fast craving release.

However, the consumer would-benefit from one product that could provide both a fast and an extended craving release of nicotine from one and the same product. In addition, a chewing gum is less expensive compare to a mouth spray delivered from a device and thus the invented product could reach more people that would like to quit smoking.

SUMMARY OF THE INVENTION

The inventors have been investigating the possibility to fuse at least one portion onto a chewing gum comprising nicotine, wherein said portion comprises nicotine bitartrate or nicotine ditartrate dihydrate. Such a portion would give an immediate release of nicotine and a faster craving relief and if a suitable buffer is used in at least one of the coatings or in another portion that the portion comprising the nicotine to provide a pH above 8, which is the pH wherein about 90% of nicotine is in the free form and able to penetrate the oral mucosa. Nicotine in another form than being free will not be able to penetrate the oral mucosa. The chewing gum should as well comprise nicotine as the conventional chewing gums present on the market today and thereby give an extended craving relief. Such a new chewing gum would generate a bi-phasic release of nicotine and help subjects that find it difficult to quit smoking with aid of conventional nicotine replacement products, such as chewing gums. The chewing gum will also be an attractive product for economical reasons as well as it will be a discreet product to use compared to some other immediate releasing nicotine products present on the market.

There are some problems connected with the manufacturing of a chewing gum having at least on portion added thereto, including finding components that could permanently adhere to the chewing gum and remain there, without influencing the consistence of the chewing gum. Components that can coexist with nicotine, are able to be heated to a degree in which the portion can be deposited onto the chewing gum before the portion becomes solidified in production scale as well as it should be enough solidified and fused onto so that it remains as a portion on the chewing gum. The portion should remain deposited without wearing off during packaging, storage and transport independent on how the chewing gum is packaged. It is important that the portion do not migrate into the chewing gum and do not affect any of the components present within the chewing gum and the different chewing gum layers.

In a first aspect the invention relates to a chewing gum comprising, at least a gum core comprising nicotine polacrilex, at least an outer coating covering the core comprising at least one sugar alcohol or mixtures thereof and at least one buffer and, at least one portion fused onto the outer coating, wherein the portion comprises nicotine bitartrate or nicotine ditartrate dihydrate and at least one sugar alcohol or a mixture of sugar alcohols. In addition, the coating and/or a portion comprises at least one buffer.

In another aspect the invention relates to a chewing gum comprising, at least a gum core comprising nicotine polacrilex, at least an inner coating covering the core comprising a film forming polymer, at least one buffer and at least one flavor, at least an outer coating covering the inner coating comprising at least one sugar alcohol or mixtures thereof and, at least one portion fused onto the outer coating, wherein the portion comprises nicotine bitartrate or nicotine ditartrate dihydrate and at least one sugar alcohol or a mixture of sugar alcohols.

At least one portion being fused onto the chewing gum, which solves the problems mentioned above and allows the production of such new chewing gums in large scale in a production plant. The new invented chewing gum provides an immediate and extended craving relief for the consumer upon use.

The at least one portion comprising nicotine will give an immediate release of nicotine and the gum core comprising nicotine polacrilex will give an extended release of nicotine, and thus the chewing gum will provide both a fast craving relief and a prolonged relief.

In another aspect the invention relates to a chewing gum as defined above having a visible, such as colored portion or portions fused onto its surface. Such a visible portion will attract the eyes of a consumer/user and for example if the color is chosen in a way to reflect speed it will affect the consumer feeling upon using such a chewing gum.

In another aspect the invention relates to a manufacturing process for the production of such a chewing gum as well as treatment of a human being suffering from cravings from tobacco dependency by the use of the new invented chewing gum.

DETAILED DESCRIPTION OF EMBODIMENTS OF THE INVENTION

Definitions

In the context of the present application and invention the following definitions apply:

The term "nicotine" refers to the amount of nicotine as the free base.

The term "portion" is intended to mean a part that is fused onto the chewing gum. It might be in any kind of form including a round portion (dot), square portion, conic portion, triangle etc. The portion may be in the form of a trade mark as well as having a color.

As used herein, the term "extended release" ("ER") refers to compositions which are characterized by that the nicotine present in the chewing gum is released over a period of at least about 30 minutes, the time a consumer normally is chewing on the gum. The release profile may be assessed via in vitro dissolution using techniques known to those skilled in the art (European Pharmacopeia 9.0, General chapters, method of analysis, 2.9.25 Dissolution for medication chewing gums, apparatus B).

The term "immediate release" ("IR") is intended to mean the release of the nicotine present in the portion within 15 minutes and the immediate release component is available for buccal absorption. The rate of release of nicotine is not prolonged by means of a controlled release matrix or other such means but it is dependent of water solubility of the polyol and nicotine. As described herein, an "immediate release" component is released as soon as the sugar alcohol and nicotine mixture is dissolved which occurs as soon as the mixture of sugar alcohol and nicotine comes in contact with saliva.

The calculation on the amount of nicotine present in the chewing gum is calculated as the free base form of nicotine.

The term "fused onto" used throughout the application is intended to be interchangeable with "attach to", "fused to", "sticked to", "deposited onto", or "adhered to".

The Chewing Gum

In one embodiment, the invention relates to a chewing gum comprising at least a gum core comprising nicotine, at least one outer coating covering the core comprising at least one sugar alcohol or mixtures thereof and at least one portion fused onto the outer coating, wherein the portion comprises nicotine or a salt thereof and at least one sugar alcohol or a mixture thereof. In addition, the coating and/or an additional portion comprises at least one buffer.

In another embodiment, the invention relates to a chewing gum comprising at least a gum core comprising nicotine. In addition, the chewing gum comprises at least one inner coating covering the core comprising a film forming polymer and at least one flavor, at least one outer coating covering the inner coating comprising at least one sugar alcohol or mixtures thereof and at least one portion fused onto the outer coating, wherein the portion comprising nicotine or a salt thereof and at least one sugar alcohol or a mixture thereof.

Chewing gums can be produced in different ways. One example is the process disclosed in the U.S. Pat. No. 5,976,581 filed already 1995, i.e., well known for a person skilled in the art how to produce a chewing gum.

The gum base core comprises nicotine, preferably in the form as a nicotine polacrilex. Nicotine is present in an amount of from about 1.0 to about 6.0 mg, about 2.0 to about 4.0 mg, such as 1.5, 2.0, 2.5, 3.0, 3.5, 4.0, 4.5, 5.0 or 5.5 calculated as per piece of gum. The nicotine will be released from the gum core when the user is chewing on the gum and the release will occur over an extended time period, normally about up to 30 minutes, which is the average time a consumer is chewing on a gum.

The gum core may be coated with an outer coating or both an inner and an outer coating.

The inner coating comprises a film forming polymer and preferably at least one flavor. The inner coating has a thickness of from about 20 to about 60 µm, such as 30 µm.

The film-forming polymers may be chosen among cellulose ethers e g hydroxy propyl methyl cellulose (HPMC), methyl hydroxy ethyl cellulose (MHEC), hydroxy propyl cellulose (HPC), hydroxyethyl cellulose (HEC), Hydroxypropyl methylcellulose phthalate, (HPMCP), ethyl hydroxyl ethyl cellulose (EHEC), and other film forming polymers such as methacrylic acid copolymer-type C sodium carboxy methyl cellulose, polydextrose, polyethylene glycols, acrylate polymers (e g poly vinyl alcohol (PVA)), polyvinyl alcohol-polyethylene glycol graft copolymers, complex of polyvinylpyrrolidone (PVP), such as povidone, polyvinyl alcohol, microcrystalline cellulose, carrageenan, pregelatinized starch, polyethylene glycol, and combinations thereof.

In one embodiment, the film-forming polymers are selected among cellulose ethers, such as hydroxy propyl methyl cellulose (HPMC), methyl hydroxy ethyl cellulose (MHEC), hydroxy propyl cellulose (HPC), hydroxyethyl cellulose (HEC), ethyl hydroxyl ethyl cellulose (EHEC). Preferably the film forming polymer is HPMC. In one embodiment, the inner coating is covered by an outer coating.

The outer coating is either covering the core or the inner coating and comprises at least one sugar alcohol or mixtures thereof. The sugar alcohol may be erythritol, maltitol, xylitol, lactitol, isomalt, mannitol, arabitol, isomalt and sorbitol or mixtures thereof. The outer coating has a thickness of from about 350 µm to about 650 µm, such as 500 µm. In one embodiment, the outer coating is a mixture of xylitol and maltitol or xylitol.

Examples of flavoring agents/flavors include, fruit and berry flavors such as lime, orange, lemon, black current, blood orange, cranberry, cloudberry, goji berry, raspberry, strawberry, wild strawberry, sea buckthorn, cherry, melon, kiwi, papaya, pineapple, passion fruit, coconut, and other flavors such as honey, herbs, the, anise, water grass, lemon grass, cooling agent, ginger, coffee, eucalyptus, mangostan, peppermint, spearmint, wintergreen, tutti-frutti, cinnamon, cacao/cocoa, vanilla, liquorice, salt, pepper, chili, menthol, aniseeds, mint or mixtures thereof. The flavoring agents/flavors may be natural extracts as well as synthetic versions as well as mixtures of flavors. The favors may be present in the gum base, inner film, outer coating as well as in the portion. Suitable examples of flavors are fruit and berry flavors, such as cool berries and different kinds of mint flavors. The flavors are preferably in the core and the inner coating or at least the inner coating.

Fused onto the outer coating is at least one portion. At least one portion comprising nicotine as a salt or a complex or mixtures thereof and at least one sugar alcohol or mixture of sugar alcohols. Nicotine in the portion is intended to include nicotine as a complex or as a salt. Numerous salts are known such as monotartrate, hydrogen tartrate, citrate, malate, hydrochloride, nicotine bitartrate or nicotine bitartrate dihydrate or nicotine polacrilex (NHT or NRC). Preferably NHT or nicotine bitartrate is present in the portion.

For example the portion may comprise a mixture of erythritol and xylitol in a proportional amount of about 90:10, 91:9, 92:8, 93:7, 96:4, 95:5, 96:4, 97:3, 98:2, 99:1 or 100:0 (% w/w of erythritol:xylithol). In another embodiment, the portion comprises at least erythritol. The nicotine is evenly distributed in the portion. Nicotine is present in the portion in an amount of about 0.25 to about 2.0 mg, such as 0.5 to about 1 mg or 0.25, 0.5, 0.75, or 1 or 1.5 mg. In addition, the portion has a weight of about 2-3% of the total weight of the chewing gum. In another embodiment, a second portion comprises at least one buffer but having the same amounts of erythritol and xylitol or erythritol as the portion comprising nicotine.

In a third embodiment the invention relates to a new chewing gum comprising at least a gum core comprising nicotine polacrilex, at least one inner coating comprising hydroxyl propyl methyl cellulose (HPMC) and at least one flavor covering the core, wherein the flavoring is selected from the group consisting of fruit and berry flavors, such as cool berries and different kinds of mint flavors, at least one outer coating covering the inner coating comprising at least xylitol and at least one portion fused onto the outer coating, wherein the portion comprising nicotine or a salt thereof, preferably NHT or nicotine bitartrate and at least erythritol. Other suitable components to be present includes gum Arabic, maize starch, titanium oxide, aroma as well as carnuba wax.

The portion may be colored. The coloring agents include lakes and dyes being approved as a food additive and examples of coloring agents are artificial colors or natural colors. One example is when the portion is defined above and may be a dot, like the dots on a lady bird.

Examples of artificial colors approved for food use in the EU include: E104: Quinoline, Yellow, E122: Carmoisine, E124: Ponceau 4R, E131: Patent Blue V and E142: Green S. In the US, the following seven artificial colorings are generally permitted in food: FD&C Blue No. 1—Brilliant Blue FCF, E133 (blue shade), FD&C Blue No. 2—Indigotine, E132 (indigo shade), FD&C Green No. 3—Fast Green FCF, E143 (turquoise shade), FD&C Red No. 3—Erythrosine, E127 (pink shade, commonly used in glace cherries), FD&C Red No. 40—Allura Red AC, E129 (red shade), FD&C Yellow No. 5—Tartrazine, E102 (yellow shade), FD&C Yellow No. 6—Sunset Yellow FCF, E110 (orange shade).

Examples of natural colors includes: Carotenoids (E160, E161, E164), chlorophyllin (E140, E141), anthocyanins (E163), and betanin (E162), Annatto (E160b), a reddish-orange dye made from the seed of the achiote, Caramel coloring (E150a-d), made from caramelized sugar, Carmine (E120), a red dye derived from the cochineal insect, *Dactylopius coccus*, Elderberry juice (E163), Lycopene (E160d), Paprika (E160c) and Turmeric (E100).

Preferably the color is a color associated with speed, such as a red or orange color.

In addition, at least one buffer is present in at least one of the gum core, inner coating, outer coating or portion. The buffer may be any suitable buffer well-known for a person skilled in the art. Examples include Sodium carbonate, Sodium bicarbonate or Potassium bicarbonate, Trometamol or mixtures thereof.

In one embodiment, the chewing gum comprises either one portion comprising nicotine or two portions attached to the coating around the gum, one including the nicotine and the other one a buffering agent being substantially free from nicotine as defined above. The buffer is present in an amount from about 1 mg to about 2.5 mg in the coating of each gum or the portion, such as from about 1.5 to about 2.5 mg in the coating of each gum or the portion, or from about 2.0 to about 2.5 mg in the coating of each gum or the portion.

In addition, the chewing gum may have at least one artificial sweetener. The artificial sweetener may be present in the gum base, inner or outer coating and/or in the portion. Examples of artificial sweeteners are saccharin, sodium saccharin, aspartame, acesulfame K, neotame, thaumatin, glycyrrhizin, sucralose, cyclamate, dihydrochalcone, alitame, miraculin and monellin and mixtures thereof.

The portion(s) may have a weight of about 1.5-3% such as 2-3%, 1.5, 2.0, 2.5, or 3.0% of the total weight of the chewing gum.

The nicotine present in the chewing gum may be in an amount from about 1.0 to about 6.0 mg, such as 1.0, 1.5, 2.0, 2.5, 3.0, 3.5, 4.0, 4.5, 5.0, 5.5, 6.0 mg and the nicotine present in the portion may be in an amount of from about 0.25 to about 1.5 mg, such as 0.3, 0.4, 0.5, 0.6, 0.7, 0.8, 0.9, 1.0, 1.1, 1.2, 1.3, 1.4 or 1.5 mg, such as 0.25 to 1.0 mg.

The Manufacturing of the Chewing Gum

Below are examples on different manufacturing processes.

In one embodiment, nicotine is mixed into a heated polyol or polyol blend. Nicotine may be in any form mentioned above. Nicotine may be melted as a part of the polyol mixture and deposited on to the gum as a solid solution.

As part of a deposited composition, the nicotine may be mixed using an inline injection and mixer system. In this system, the nicotine is not exposed to temperatures exceeding 125° C. for an extended period of time as part of the deposition mixture, preferably not more than 30 minutes, or more preferably not more than 1 hour. In another embodiment, the nicotine is exposed to temperatures exceeding 115° C. for not more than 1 hour.

In another embodiment, the deposited gum is prepared using multiple deposition steps, for instance at least two steps in order to deposit more than one composition. These steps may include two or more deposition nozzles and two or more mixing chambers. In one embodiment, the inner mixture comprises a nicotine based formulation, and outer mixture comprises a non-nicotine based formulation.

In one embodiment, the two portions of the deposition are on top of each other. In another embodiment, the two portions of the deposition are adjacent to each other on one face of the gum. In another embodiment, the first portion partially covers one face of the gum. In another embodiment, the nicotine is incorporated into a solvent based system, wherein the solvent is dried after deposition. The solvent may include water or an organic solvent such as ethanol, isopropanol or mixtures thereof.

Further the nicotine portion may be created by utilization of techniques such as 2D or 3D printing, being well known for a person skilled in the art.

Finally, the invention relates to the of the chewing gum for the treatment of a human being suffering from cravings from tobacco dependency.

EXAMPLES

Example 1

Chewing gum base was obtained from a chewing gum base producer and preparation of chewing gums with nicotine polacrilex was made according to the process disclosed in WO2006/124366. However, the polymer coating was not used for some of the batches as well as in some a buffer were included in the polymer coating solution.

The following formulation were used for the polymer coating.

| Sub Coating Solution | Unit Formula mg/gum | "Dry" % | Wet % | Weight for 400 g Coating solution |
|---|---|---|---|---|
| Metocel HPMC E3/K3 | 7.5 | 32.6% | 12.7% | 50.9 g |
| Polysorbate 80 | 0.5 | 2.2% | 0.8% | 3.4 g |
| Sucralose | 5 | 21.7% | 8.5% | 33.9 g |
| Tuti Frutti | 9 | 39.1% | 15.3% | 61.0 g |
| Sodium carbonate | 1 | 4.3% | 1.7% | 6.8 g |
|  | 0 | 0.0% | 0.0% | 0.0 g |
|  | 0 | 0.0% | 0.0% | 0.0 g |

| Sub Coating Solution | Unit Formula mg/gum | "Dry" % | Wet % | Weight for 400 g Coating solution |
|---|---|---|---|---|
| Sum "Dry" Exipients | 23 | 100.0% | 39.0% | 156.0 g |
| Aqua pur | 36.0 |  | 61.0% | 244.0 g |
| Sum Sub Coating Solution | 59.0 |  |  |  |
| Sum Wet % |  |  | 100.0% | 400 g |
| Dry Content |  |  | 39.0% |  |
| Metocel HPMC E3/K3 | 7.5 | 30.6% | 11.9% | 47.8 g |
| Polysorbate 80 | 0.5 | 2.0% | 0.8% | 3.2 g |
| Sucralose | 5 | 20.4% | 8.0% | 31.8 g |
| Tutti Frutti | 9 | 36.7% | 14.3% | 57.3 g |
| Sodium Carbonate | 2.5 | 10.2% | 4.0% | 15.9 g |
|  | 0 | 0.0% | 0.0% | 0.0 g |
|  | 0 | 0.0% | 0.0% | 0.0 g |
| Sum "Dry" Exipients | 24.5 | 100.0% | 39.0% | 156.0 g |
| Aqua pur | 38.3 |  | 61.0% | 244.0 g |
| Sum Sub Coating Solution | 62.8 |  |  |  |
| Sum Wet % |  |  | 100.0% | 400 g |
| Dry Content |  |  | 39.0% |  |

Example 2

Evaluation of different combinations of ingredients in the portion to be fused onto the chewing gum. Table A to F.

TABLE A

| | Initial Experiments | | | | | | | | |
|---|---|---|---|---|---|---|---|---|---|
| Sample | 1 | 2 | 3 | 4 | 5 | 6 | 7 | 8 | 9 |
| Nicotine Bitartrate | 10.00 | 10.00 | 10.00 | 20.00 | 10.00 | 10.00 | 10.00 | 10.00 | 10.00 |
| Xylitol | 90.00 |  | 45.00 |  |  |  |  |  | 90.00 |
| Xylitol with Dextrin |  | 90.00 |  |  |  |  |  |  |  |
| Sorbitol |  |  | 45.00 |  |  |  |  |  |  |
| Erythritol |  |  |  |  |  |  |  |  |  |
| Dye | q.s. | q.s. | q.s. | q.s. | q.s. | q.s. | q.s. |  |  |
| Precirol ®[a] |  |  |  | 70.00 | 90.00 |  |  |  |  |
| Gelucire ®[b] |  |  |  |  |  |  | 90.00 |  |  |
| XylitolDC |  |  |  |  |  |  |  |  | 90.00 |
| Trehalose Dihydrate |  |  |  |  |  |  |  | 90.00 |  |

[a]Glyceryl distearate NF/Glyceryl palmitostearate commercially available from Gattefosse Corporation
[b]Lauroyl polyoxyl-32 glycerides commercially available from Gattefosse Corporation Result. Among the combinations present in Table A, samples 2, 5 and 6 seem to be the best ones.

TABLE B

| | Seeding Experiments | | | | | | | | |
|---|---|---|---|---|---|---|---|---|---|
| Sample | 1 | 2 | 3 | 4 | 5 | 6 | 7 | 8 | 9 |
| Nicotine Bitartrate | 10.00 | 10.00 | 10.00 | 10.00 | 10.00 | 10.00 | 10.00 | 10.00 | 10.00 |
| XylitolDC | 85.00 | 85.00 |  |  |  |  | 81.00 |  |  |
| Xylitol |  |  | 85.00 | 85.00 | 85.00 | 85.00 |  | 81.00 | 81.00 |
| Mannitol[1] | 5.00 |  |  |  |  |  | 9.00 |  |  |
| Syloid 63FP |  | 5.00 | 5.00 |  |  |  |  | 9.00 |  |
| Neusilin UFL2 |  |  |  | 5.00 |  |  |  |  |  |
| Erythritol Powder |  |  |  |  | 5.00 |  |  |  |  |

TABLE B-continued

| Seeding Experiments | | | | | | | | | |
|---|---|---|---|---|---|---|---|---|---|
| Sample | 1 | 2 | 3 | 4 | 5 | 6 | 7 | 8 | 9 |
| Dye | q.s. | q.s. | q.s. | q.s. | q.s. | q.s. | q.s. | q.s. | q.s. |
| Titanium Dioxide | q.s. | q.s. | q.s. | q.s. | q.s. | 5.00 | q.s. | q.s. | q.s. |
| Isomalt | | | | | | | | | 9.00 |
| Temperature of Blend (° C.) | 88.5 | 87.0 | 86.0 | 92.0 | 92.0 | 90.0 | 110.0 | 110.0 | 100.0 |

[1]All materials at 5% of the composition were intentionally added to induce solidification
Syloid 63FP: Colloidal Hydrated Silica commercially available from the Grace Corporation
Neusilin UFL2: Magnesium Aluminumetasilicate commercially available from Fuji Chemicals Result. Among the combinations present in Table B, samples 3, 7 and 8 seem to be the best ones.

TABLE C

| Further experiments | | | | | | | | |
|---|---|---|---|---|---|---|---|---|
| Sample | 1 | 2 | 3 | 4 | 5 | 6 | 7 | 8 |
| Nicotine Bitartrate | 10.00 | 10.00 | 10.00 | 10.00 | 10.00 | 10.00 | 10.00 | 10.00 |
| polyglycitol powder | 5.00 | 5.00 | 5.00 | | | | | |
| XylitolDC | 85.00 | | | | | | 87.00 | 82.00 |
| Xylitol | | 85.00 | | 87.00 | 74.00 | | | |
| Erythritol | | | 85.00 | | | 85.00 | | |
| Dye | q.s. | q.s. | q.s. | q.s. | q.s. | q.s. | | |
| Titanium Dioxide | q.s. | q.s. | q.s. | q.s. | | | 2.50 | 2.50 |
| Sodium Carbonate anhydrous (buffer) | | | | 2.00 | 16.00 | | | |
| Tris (buffer) | | | | | | 5.00 | | |
| Sucralose | | | | | | | 0.50 | 0.50 |
| Syloid[b] | | | | | | | | 5.00 |

[b]Commercially available from the Grace Corporation

Result. Among the combinations present in Table C, samples 3 and 6 seem to be the best ones.

TABLE D

| Further experiments | | | | | | | |
|---|---|---|---|---|---|---|---|
| Sample | 1 | 2 | 3 | 4 | 5 | 6 | 7 |
| Nicotine Bitartrate | 15.00 | 15.00 | 5.00 | 15.00 | 10.00 | 10.00 | 10.00 |
| Xylitol | 83.25 | 83.75 | 92.50 | | 5.00 | 5.00 | 10.00 |
| D-Sorbitol | | | | 82.00 | | | |
| Erythritol | | | | | 82.50 | 81.50 | 77.50 |
| Dye | q.s. | q.s. | q.s. | q.s. | q.s. | q.s. | q.s. |
| Titanium Dioxide | 1.25 | 1.25 | 2.50 | 2.50 | 2.50 | 2.50 | 2.50 |
| Sucralose | 0.50 | | | 0.50 | | | |
| Poloxamer | | | | | | | 1.00 |

Result. Among the combinations present in Table D, samples 5, 6 and 7 seem to be the best ones.

TABLE E

| | Additional Seeding Examples | | | | | | | | |
|---|---|---|---|---|---|---|---|---|---|
| Sample | 1 | 2 | 3 | 4 | 5 | 6 | 7 | 8 | 9 |
| Nicotine Bitartrate | 10.00 | 10.00 | 10.00 | 10.00 | 10.00 | 10.00 | 10.00 | 10.00 | 10.00 |
| Amberlite IRP69 | 2.50 | | | | | | | | |
| Xylitol$^c$ | 86.50 | 86.50 | 85.00 | 85.00 | 89.00 | 89.00 | 89.00 | 89.00 | 79.75 |
| XylitolDC$^c$ sprinkled | | | | | q.s. | | | | |
| Erythritol sprinkled | | | | | | q.s. | | | |
| Dye | q.s. | q.s. | q.s. | q.s. | q.s. | q.s. | q.s. | | |
| Titanium Dioxide | 1.00 | 1.00 | | | 1.00 | 1.00 | 1.00 | 1.00 | 0.25 |
| Sodium Citrate Anhydrous | | 2.50 | | | | | | | |
| Soluplus ®$^b$ | | | 5.00 | | | | | | |
| Talc | | | | 5.00 | | | | | |
| Talc sprinkled | | | | | | | q.s. | | |
| Syloid sprinkled | | | | | | q.s. | | | |
| Mannitol (Pearlitol ® 25 C.) | | | | | | | | | 10.00 |
| Ethanol sprayed | | | | | | | | q.s. | |

$^b$polyvinyl caprolactam-polyvinyl acetate-polyethylene glycol graft copolymer commercially available from the BASF corporation "sprinkled" and "sprayed": indicates small amount added to surface to induce solidification.

Result. Among the combinations present in Table E, samples 5, 6, 7 and 8 seem to be the best ones.

| | Example Summary: Table F: Solvent Based Formulas | | | | | | |
|---|---|---|---|---|---|---|---|
| Sample | 1 | 2 | 3 | 4 | 5 | 6 | 7 |
| Solution Composition (%) | | | | | | | |
| Nicotine Bitartrate | 2.22 | 5.00 | 3.00 | 4.00 | 10.00 | 7.00 | 4.00 |
| Ethanol | 57.78 | 75.00 | 65.00 | | | | |
| Water | 19.99 | | | 35.10 | 24.00 | 65.00 | 33.00 |
| Hydroxypropylcellulose | 20.00 | 20.00 | 28.00 | | | 28.00 | |
| Hydrogen Starch Hydrosylate | | | | 60.90 | 72.00 | | |
| Xylitol | | | | | | | 63.00 |
| Amount of solution added (mg) | 135.00 | 60.00 | 42.86 | 75.03 | 75.03 | 72.87 | |
| Weight of dried film (mg) | 30.00 | 15.00 | 15.00 | 48.70 | 57.03 | 15.00 | |

Example Summary: Table F: Solvent Based Formulas

| Sample | 1 | 2 | 3 | 4 | 5 | 6 | 7 |
|---|---|---|---|---|---|---|---|
| Dose of dried NHT | 3.00 | 3.00 | 3.00 | 3.00 | 3.00 | 3.00 | |
| Conclusion | Worked | Worked | Worked | Worked | Worked | Did not work | Did not work |

Note:
Ethanol and Water dried and removed from the solution following deposition Result. Among the combinations present in Table F, samples 1-5 seem to be the best ones.

Example 3

Preparation of Different Portions Containing Nicotine and Excipient.

| Examples | 1 | 2 | 3 | 4 | 5 | 6 | 7 | 8 | 9 | 10 | 11 |
|---|---|---|---|---|---|---|---|---|---|---|---|
| APIs | | | | | | | | | | | |
| Nicotine Polacrilex | | | | | 25 | 12.5 | | | | | |
| Nicotine Bitartrate Dihydrate | 15.39 | | 15.4 | | 7.15 | 14.3 | 14.3 | 14.3 | 14.3 | 14.3 | 7.13 |
| Nicotine free base | | 5 | | | | | | | | | |
| Excipients | | | | | | | | | | | |
| Xylitol | | 93 | 82.8 | 73 | 78.4 | 80.4 | | 82.4 | 20.0 | 3.9 | |
| Isomalt | 84.61 | | | | | | | | | | |
| Erythritol | | | | | | 3.3 | 83.7 | | 65.7 | 79.8 | 92.7 |
| Dye | q.s. | q.s. | q.s. | q.s. | q.s. | q.s. | q.s. | q.s. | q.s. | q.s. | q.s. |
| Mannitol 25 μ | | | | | | | | 3.3 | | | |
| Sodium Carbonate | | | | | | | | | | | |
| Neotame | | | | | | | | | | | 0.15 |
| Titanium dioxide | | 2 | 1.8 | 2 | 2 | 2.0 | 2.0 | | | 2 | |

Amounts expressed in % w/w per API and excipient, different batch sizes used
q.s. = quantum satis, sufficient amount

Example 4

Buffer-Containing Portions.

Amounts expressed in % w/w per excipient per batch

| Example | 1 | 2 | 3 | 4 | 5 | 6 | 7 | 8 |
|---|---|---|---|---|---|---|---|---|
| Erythritol | 29.50 | 29.250 | 28.875 | 28.50 | 29.250 | 28.50 | 28.875 | 28.50 |
| Sodium Carbonate anhydrous | 0.50 | 0.750 | 1.125 | 1.50 | | | | |
| Sodium Bicarbonate | | | | | 0.750 | 1.50 | | |
| Potassium Carbonate | | | | | | | 1.125 | |
| Trometamol | | | | | | | | 1.50 |

Procedure: all starting materials, polyol or mixtures of several polyols, nicotine source or combinations thereof, dye and seeding agent where mixed in a glass beaker. The mixture was heated until melting under stirring of all the components except for titanium dioxide. 20 mg of the melted mass was deposited on the coated gum with aid of a micropipette. The droplet was occasionally flattened with a heated tool directly after deposition to reduce the thickness of the deposited droplet.

Example 5

Application of the different portions prepared in EXAMPLE 3 on chewing gums prepared in EXAMPLE 1. 20 mg of the mixture (EXAMPLE 1-12) was applied to the surface of each of the chewing gums. The portions were allowed to solidify. The chewing gums were analyzed for speed of solidification. The chewing gums were also analyzed for the release characteristics to show a fast and extended release profile using the method in the European Pharmacopeia 9.0, General chapters, method of analysis, 2.9.25 Dissolution for medication chewing gums, apparatus B.

The invention claimed is:
1. A chewing gum comprising:
 a gum core comprising nicotine polacrilex,
 an outer coating covering the gum core wherein the outer coating comprises at least one sugar alcohol, and
 a portion fused onto the outer coating, wherein the portion comprises nicotine bitartrate or nicotine ditartrate dihydrate and at least one sugar alcohol, and wherein the portion is in a form consisting of a round portion, a square portion, a conic portion, a triangle portion or a trade mark.

2. The chewing gum of claim 1, further comprising at least one buffer in the outer coating or in the portion fused onto the outer coating.

3. The chewing gum of claim 1, further comprising an inner coating between the gum core and the outer coating wherein the inner coating comprises a film forming polymer, at least one flavor and at least one buffer.

4. The chewing gum of claim 1, wherein the portion fused onto the outer coating provides an immediate release of nicotine and the gum core provides an extended release of nicotine.

5. The chewing gum of claim 1, wherein the at least one sugar alcohol in the outer coating is selected from the group consisting of erythritol, xylitol, lactitol, mannitol, maltitol, isomalt, arabitol and sorbitol.

6. The chewing gum of claim 5, wherein the at least one sugar alcohol in the outer coating is xylitol, maltitol or mixtures thereof.

7. The chewing gum of claim 6, wherein the at least one sugar alcohol in the outer coating is xylitol.

8. The chewing gum of claim 1, wherein the at least one sugar alcohol in the portion fused onto the outer coating is erythritol and xylitol or erythritol.

9. The chewing gum of claim 8, wherein the at least one sugar alcohol in the portion fused onto the outer coating is erythritol.

10. The chewing gum of claim 1, further comprising at least one artificial sweetener.

11. The chewing gum of claim 3, wherein the inner coating further comprises at least one artificial sweetener.

12. The chewing gum of claim 1, wherein the portion further comprises at least one coloring agent.

13. The chewing gum of claim 1, further comprising a second portion fused onto the outer coating.

14. The chewing gum of claim 13, wherein nicotine is present in the portion fused onto the outer coating and at least one buffer is present in the second portion fused onto the outer coating.

15. The chewing gum of claim 1, wherein the portion fused onto the outer coating comprises nicotine and at least one buffer.

16. The chewing gum of claim 1, wherein the outer coating further comprises at least one buffer.

17. The chewing gum of claim 1, further comprising an inner coating between the gum core and the outer coating wherein the inner coating comprises a film forming polymer and at least one flavor.

18. The chewing gum of claim 1, wherein the portion has a weight of about 1-3% of the total weight of the chewing gum.

19. The chewing gum of claim 1, wherein the gum core contains nicotine polacrilex in an amount of from about 1.0 mg to about 6.0 mg and the portion contains nicotine bitartrate or nicotine ditartrate dihydrate in an amount of from about 0.25 mg to about 1.5 mg.

20. The chewing gum of claim 1, further comprising at least one buffering agent.

21. A method of treating a human suffering from cravings from tobacco dependency, comprising: administering to the human a chewing gum comprising a gum core comprising nicotine polacrilex, an outer coating covering the gum core wherein the outer coating comprises at least one sugar alcohol, and a portion fused onto the outer coating, wherein the portion comprises nicotine bitartrate or nicotine ditartrate dihydrate and at least one sugar alcohol, and wherein the portion is in a form consisting of a round portion, a square portion, a conic portion, a triangle portion or a trade mark.

22. The chewing gum of claim 1, wherein the portion is in the form of a round portion.

* * * * *